United States Patent
Katsuyama

(10) Patent No.: US 10,463,344 B2
(45) Date of Patent: Nov. 5, 2019

(54) ULTRASOUND DIAGNOSTIC APPARATUS AND SIGNAL PROCESSING METHOD THEREOF FOR DETERMINING AN AMBIENT SOUND VELOCITY

(71) Applicant: FUJIFILM Corporation, Tokyo (JP)

(72) Inventor: Kimito Katsuyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/938,748

(22) Filed: Jul. 10, 2013

(65) Prior Publication Data

US 2013/0303912 A1 Nov. 14, 2013

Related U.S. Application Data

(63) Continuation of application No. 12/923,602, filed on Sep. 29, 2010, now abandoned.

(30) Foreign Application Priority Data

Sep. 30, 2009 (JP) .................................. 2009-227225
Mar. 31, 2010 (JP) .................................. 2010-081053

(51) Int. Cl.
*A61B 8/00* (2006.01)
*A61B 8/08* (2006.01)
(Continued)

(52) U.S. Cl.
CPC .............. *A61B 8/4488* (2013.01); *A61B 8/08* (2013.01); *A61B 8/145* (2013.01); *A61B 8/4444* (2013.01);
(Continued)

(58) Field of Classification Search
USPC ....................................................... 600/443
See application file for complete search history.

(56) References Cited

U.S. PATENT DOCUMENTS 5,415,173 A 5/1995 Miwa et al.
6,629,929 B1 * 10/2003 Jago et al. ..................... 600/447
(Continued)

FOREIGN PATENT DOCUMENTS

JP 63-082633 A 4/1988
JP 08-317926 A 12/1996
(Continued)

OTHER PUBLICATIONS

D. Napolitano et al., Sound speed correction in ultrasound imaging, e43-e46, Ultrasonics 44, Mountain View CA, USA, Jul. 20, 2006.
(Continued)

*Primary Examiner* — Amelie R Gillman
(74) *Attorney, Agent, or Firm* — Edwards Neils LLC; Jean C. Edwards, Esq.

(57) ABSTRACT

The presently disclosed subject matter is intended to correctly determine an ambient sound velocity at each level of pixels or line images constituting an ultrasound image, and construct a high-precision ultrasound image. A region-of-interest setting unit sets a region of interest on an ultrasound image. A transmission focus control unit gives a transmission focus instruction, so that a transmitting circuit performs transmission focusing on the region of interest. A set sound velocity specification unit specifies a set sound velocity used to perform reception focusing on RF data. A focus index calculation unit performs reception focusing on the RF data for each of a plurality of set sound velocities to calculate the focus index of the RF data. An ambient sound velocity determination unit determines the ambient sound velocity of the region of interest on the basis of the focus index for each of the plurality of set sound velocities.

4 Claims, 11 Drawing Sheets

(51) Int. Cl.
  *G01N 29/06* (2006.01)
  *G01N 29/44* (2006.01)
  *A61B 8/14* (2006.01)

(52) U.S. Cl.
  CPC ....... *A61B 8/5207* (2013.01); *G01N 29/0654* (2013.01); *G01N 29/4463* (2013.01); *G01N 2291/0289* (2013.01); *G01N 2291/02475* (2013.01)

(56) References Cited

U.S. PATENT DOCUMENTS

| | | | |
|---|---|---|---|
| 2003/0092990 A1 | 5/2003 | Baba et al. | |
| 2006/0235302 A1 | 10/2006 | Grossman et al. | |
| 2007/0083110 A1 | 4/2007 | Lin et al. | |
| 2007/0232925 A1* | 10/2007 | Satoh | A61B 5/02007 600/459 |
| 2007/0239007 A1* | 10/2007 | Silverman | A61B 8/08 600/437 |
| 2008/0242999 A1* | 10/2008 | Kakee | 600/458 |
| 2009/0003128 A1 | 1/2009 | Jeong et al. | |
| 2009/0093721 A1 | 4/2009 | Katsuyama | |
| 2009/0292207 A1 | 11/2009 | Karasawa | |

FOREIGN PATENT DOCUMENTS

| | | |
|---|---|---|
| JP | 2001-252276 A | 9/2001 |
| JP | 2001-276064 A | 10/2001 |
| JP | 2005-177336 A | 7/2005 |
| JP | 2007-007045 A | 1/2007 |
| JP | 2009-022656 A | 2/2009 |
| JP | 2009-034262 A | 2/2009 |
| JP | 2009-090102 A | 4/2009 |
| JP | 2009-101145 A | 5/2009 |
| JP | 2009-279306 A | 12/2009 |

OTHER PUBLICATIONS

Partial translation of JP 63-82633, Pub. Date Apr. 13, 1998.
Notification of Reasons for Rejection issued by JPO dated Jun. 28, 2013 in connection with Japanese Patent Application No. 2010-081053, from which the present app. claims priority.
Notification of Reasons for Rejection issued by JPO dated Jun. 20, 2014 in connection with corresponding Japanese Patent Application No. 2013-124672.
Notification of Reasons for Rejection issued by JPO dated Jun. 23, 2014 in connection with corresponding Japanese Patent Application No. 2013-124673.
Extended European Search Report issued by EPO dated Aug. 26, 2013, in connection with corresponding European Patent Application No. 13173606.8.
Extended European Search Report issued by EPO dated Aug. 26, 2013, in connection with corresponding European Patent Application No. 13173607.6.
Extended European Search Report issued by EPO dated Aug. 26, 2013, in connection with corresponding European Patent Application No. 13173604.3.

* cited by examiner

ULTRASOUND DIAGNOSTIC APPARATUS AND SIGNAL PROCESSING METHOD THEREOF FOR DETERMINING AN AMBIENT SOUND VELOCITY

CROSS-REFERENCE TO RELATED APPLICATIONS

This application is a continuation application of U.S. patent application Ser. No. 12/923,602, filed Sep. 29, 2010, which claims priority from Japanese Patent Application Nos. 2009-227225, filed Sep. 30, 2009, and 2010-081053, filed Mar. 31, 2010, the contents of all of which are herein incorporated by reference in their entirety.

BACKGROUND OF THE INVENTION

Field of the Invention

The presently disclosed subject matter relates to an ultrasound diagnostic apparatus and the signal processing method thereof for taking and displaying ultrasound images of a region under diagnosis of an object by utilizing ultrasound waves, and more particularly, to an ultrasound diagnostic apparatus and the signal processing method thereof for correcting the ambient sound velocity of the region under diagnosis.

Description of the Related Art

Conventionally, an ultrasound diagnostic apparatus for taking and displaying ultrasound images of a region under diagnosis of an object by utilizing ultrasound waves has been composed of a probe, an ultrasound transmitter/receiver unit, an image processing circuit, a digital scan converter (DSC), an image display unit, and the like.

In such a conventional ultrasound diagnostic apparatus, an ultrasound velocity value set for the apparatus as a whole is fixed to a certain value.

Since the velocity of sound varies due to a difference in tissues, such as a fat layer and a muscle layer, within a living body, the velocity of ultrasound waves (hereinafter referred to as an ambient sound velocity) within an object is not uniform. In addition, since the fat examinee and the thin examinee differ in the thickness of a fat layer and a muscle layer, an examinee-by-examinee ambient sound velocity varies between individuals.

As described above, in the conventional ultrasound diagnostic apparatus, the value of an ultrasound velocity set for the apparatus as a whole (hereinafter referred to as a set sound velocity) is fixed to a certain value. Consequently, the arrival time of a reflected wave deviates more largely from a delay time set in an ultrasound transmitter/receiver unit in proportion to an increase in the deviation of an ambient sound velocity within an object from the set sound velocity. Thus, the degree of focusing degrades, and therefore, the quality of an obtained ultrasound image degrades.

Hence, an ultrasound diagnostic apparatus, in which a set sound velocity set therein is made adjustable to improve focusing, is proposed in Japanese Patent Application Laid-Open No. 8-317926, and the like.

In the ultrasound diagnostic apparatus of this Japanese Patent Application Laid-Open No. 8-317926, a focus calculation circuit, which is provided between a control circuit section and an ultrasound transmitter/receiver unit, calculates a focus by using an ultrasound velocity value input from an operating input unit as a set sound velocity of the entire apparatus. And, a focus data storage circuit, which is provided in a stage following the focus calculation circuit, records focus data calculated by the focus calculation circuit and reads out the focus data to send to the ultrasound transmitter/receiver unit. An ultrasound image is taken using this focus data which is read out from the focus data storage circuit. Thereby, the ultrasound diagnostic apparatus is configured to perform correction of the set sound velocity.

In addition, the ultrasound diagnostic apparatus of this Japanese Patent Application Laid-Open No. 8-317926 is provided with a spatial frequency analysis circuit for analyzing a spatial frequency with regard to the amplitude of an ultrasound reception signal, using an output signal from the ultrasound transmitter/receiver unit as an input. In the ultrasound diagnostic apparatus, while taking ultrasound images by using focus data read out of the focus data storage circuit, the spatial frequency analysis circuit determines an ultrasound velocity value at which the high-frequency component or the variance of the spatial frequency is maximum with regard to the amplitude of the ultrasound reception signal, and feeds back this spatial frequency analysis signal to the control circuit section. Thereby, the ultrasound diagnostic apparatus can correct the set sound velocity by this ultrasound velocity value.

SUMMARY OF THE INVENTION

However, in the ultrasound diagnostic apparatus of Japanese Patent Application Laid-Open No. 8-317926, the high-frequency component or the variance of the spatial frequency is calculated with regard to the amplitude of the ultrasound reception signal by the spatial frequency analysis circuit, for example, while taking ultrasound images by using the focus data read out from the focus data storage circuit.

Consequently, in order to correct the previously set sound velocity, captured and constructed ultrasound images need to be used. That is, since the spatial frequency of an entire ultrasound image is analyzed, the set sound velocity is merely corrected to the ambient sound velocity of the entire ultrasound image. Thus, it is not possible to appropriately correct the set sound velocity to, for example, an ambient sound velocity at each level of pixels or line images constituting the ultrasound image. Accordingly, it is not possible to construct a high-precision ultrasound image.

The presently disclosed subject matter has been accomplished in view of such circumstances as described above. An object of the presently disclosed subject matter therefore is to provide an ultrasound diagnostic apparatus and the signal processing method thereof capable of correctly determining an ambient sound velocity at each level of pixels or line images constituting an ultrasound image, and constructing a high-precision ultrasound image.

In order to achieve the aforementioned object, an ultrasound diagnostic apparatus according to a first aspect of the presently disclosed subject matter is configured by including: an ultrasound probe including a plurality of ultrasound transducers for transmitting ultrasound waves to an object and receiving ultrasound waves reflected by the object to output an ultrasound detection signal; a region-of-interest setting device which sets a region of interest within the object; a transmission focus instruction device which causes the ultrasound probe to bring the ultrasound waves into transmission focus on the region of interest; a set sound velocity specification device which specifies a plurality of set sound velocities used to perform reception focusing on the ultrasound detection signal from the region of interest; a focus index calculation device which calculates the focus index of the ultrasound detection signal for each of the plurality of set sound velocities by performing the reception focusing; and an ambient sound velocity determination device which determines the ambient sound velocity of the region of interest on the basis of the focus index for each of the plurality of set sound velocities.

In the ultrasound diagnostic apparatus according to the first aspect, the region-of-interest setting device sets a region of interest within the object; the transmission focus instruction device causes the ultrasound probe to bring the ultrasound waves into transmission focus on the region of interest; the set sound velocity specification device specifies a plurality of set sound velocities used to perform reception focusing on the ultrasound detection signal from the region of interest; the focus index calculation device calculates the focus index of the ultrasound detection signal for each of the plurality of set sound velocities by performing the reception focusing; and the ambient sound velocity determination device determines the ambient sound velocity of the region of interest on the basis of the focus index for each of the plurality of set sound velocities, thereby correctly determining an ambient sound velocity at each level of pixels or line images constituting an ultrasound image and enabling the construction of a high-precision ultrasound image.

As with an ultrasound diagnostic apparatus according to a second aspect of the presently disclosed subject matter, the ultrasound diagnostic apparatus according to the first aspect is preferably such that the focus index is at least one of an integration value, a square integration value, a peak value, a contrast value, or a half bandwidth, a frequency-spectral integration value or square integration value, a square sum normalized by a mean value, a frequency-spectral half bandwidth, a frequency-spectral integration value or square integration value normalized by a maximum value or a direct current component, and an autocorrelation value of the ultrasound detection signal.

As with an ultrasound diagnostic apparatus according to a third aspect of the presently disclosed subject matter, the ultrasound diagnostic apparatus according to the first aspect is preferably such that the focus index is an index which does not include the intensity information of the ultrasound detection signal but is based only on the frequency spectrum information.

As with an ultrasound diagnostic apparatus according to a fourth aspect of the presently disclosed subject matter, the ultrasound diagnostic apparatus according to the first or second aspect is preferably such that the index based only on the frequency spectrum information is at least one of a square sum normalized by a mean value, a frequency-spectral integration value or square integration value normalized by a maximum value or a direct current component, an autocorrelation value, and a frequency-spectral half bandwidth.

As with an ultrasound diagnostic apparatus according to a fifth aspect of the presently disclosed subject matter, the ultrasound diagnostic apparatus according to the first aspect is preferably such that the focus index is an index multiplied by such a coefficient as to become smaller in value toward the peripheral portions of an image generated by performing reception focusing on the ultrasound detection signal.

As with an ultrasound diagnostic apparatus according to a sixth aspect of the presently disclosed subject matter, the ultrasound diagnostic apparatus according to the first aspect is preferably such that a determination is made as to whether or not any structural object is included in the region of interest, so that the ambient sound velocity is determined using a focus index according to the result of the determination.

As with an ultrasound diagnostic apparatus according to a seventh aspect of the presently disclosed subject matter, the ultrasound diagnostic apparatus according to the sixth aspect is preferably such that the focus index utilizes a line image when a determination is made as to whether or not any structural object is included in the region of interest and if a structural object is not included therein, and is based only on the frequency spectrum information of the ultrasound detection signal without including the intensity information thereof.

As with an ultrasound diagnostic apparatus according to an eighth aspect of the presently disclosed subject matter, the ultrasound diagnostic apparatus according to the sixth aspect is preferably such that the focus index utilizes a line-by-line common image when a determination is made as to whether or not any structural object is included in the region of interest and if a structural object is included therein, and is based only on the intensity information of the line-by-line common image without including the frequency spectrum information thereof.

As with an ultrasound diagnostic apparatus according to a ninth aspect of the presently disclosed subject matter, the ultrasound diagnostic apparatus according to the eighth aspect is preferably such that the index based only on the intensity information is at least one of an integration value, a square integration value, a peak value, and a frequency-spectral integration value or square integration value.

As with an ultrasound diagnostic apparatus according to a tenth aspect of the presently disclosed subject matter, the ultrasound diagnostic apparatus according to any one of the first to ninth aspects preferably further includes an ultrasound image construction device which constructs an ultrasound image of the region of interest on the basis of the ambient sound velocity.

As with an ultrasound diagnostic apparatus according to an eleventh aspect of the presently disclosed subject matter, the ultrasound diagnostic apparatus according to any one of the first to tenth aspects is preferably such that the region of interest set by the region-of-interest setting device is a point reflection region on a sound ray region within the object.

As with an ultrasound diagnostic apparatus according to a twelfth aspect of the presently disclosed subject matter, the ultrasound diagnostic apparatus according to any one of the first to eleventh aspects is preferably such that the region of interest set by the region-of-interest setting device is a one-sound ray region within the object.

As with an ultrasound diagnostic apparatus according to a thirteenth aspect of the presently disclosed subject matter, the ultrasound diagnostic apparatus according to the twelfth aspect is preferably such that the region of interest set by the region-of-interest setting device is a two-dimensional region including a plurality of the one-sound ray regions.

A signal processing method of an ultrasound diagnostic apparatus according to a fourteenth aspect of the presently disclosed subject matter includes: a region-of-interest setting step of setting a region of interest within an object; a transmission focus instruction step of causing an ultrasound probe to bring ultrasound waves into transmission focus on the region of interest; a set sound velocity specification step of specifying a plurality of set sound velocities used to perform reception focusing on an ultrasound detection signal from the region of interest; a focus index calculation step of calculating the focus index of the ultrasound detection signal for each of the plurality of set sound velocities by performing the reception focusing; and an ambient sound velocity determination step of determining the ambient sound velocity of the region of interest on the basis of the focus index for each of the plurality of set sound velocities.

As with a signal processing method of an ultrasound diagnostic apparatus according to a fifteenth aspect of the presently disclosed subject matter, the signal processing method of an ultrasound diagnostic apparatus according to the fourteenth aspect is preferably such that the focus index is at least one of an integration value, a square integration value, a peak value, a contrast value, a half bandwidth, a frequency-spectral integration value or square integration value, a square sum normalized by a mean value, a frequency-spectral half bandwidth, a frequency-spectral integration value or square integration value normalized by a maximum value or a direct current component, and an autocorrelation value of the ultrasound detection signal.

As with a signal processing method of an ultrasound diagnostic apparatus according to a sixteenth aspect of the presently disclosed subject matter, the signal processing method of an ultrasound diagnostic apparatus according to the fourteenth or fifteenth aspect preferably further includes an ultrasound image construction step of constructing an ultrasound image of the region of interest on the basis of the ambient sound velocity.

As has been described heretofore, according to the presently disclosed subject matter, there is provided an advantageous effect of being able to correctly determine an ambient sound velocity at each level of pixels or line images constituting an ultrasound image, and constructing a high-precision ultrasound image.

DETAILED DESCRIPTION OF THE PREFERRED EMBODIMENTS

Hereinafter, an ultrasound diagnostic apparatus and the signal processing method thereof according to the presently disclosed subject matter will be described in detail for each embodiment with reference to the accompanying drawings.

First Embodiment

Figure 1:
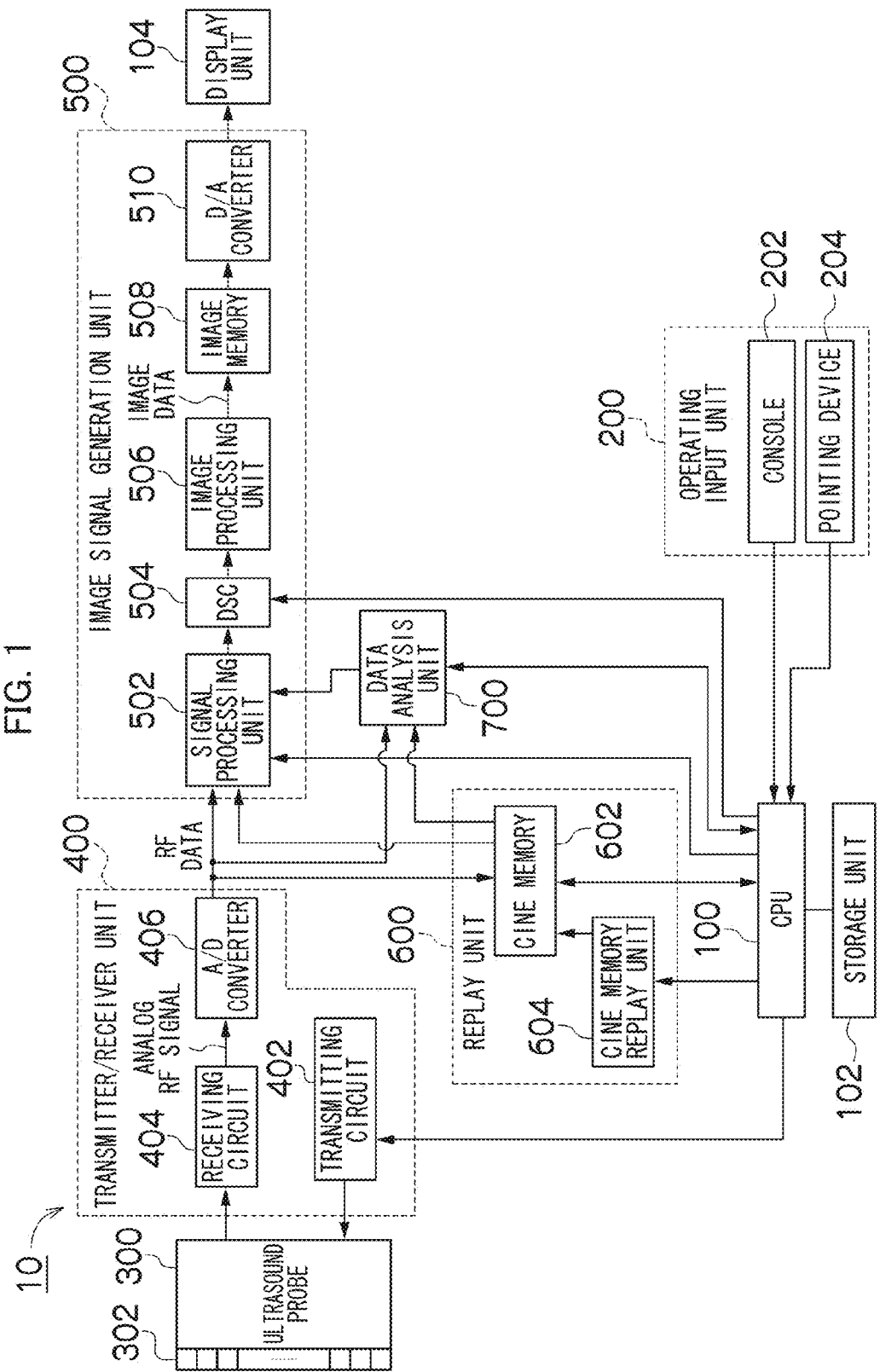
FIG. 1 is a block diagram illustrating an ultrasound diagnostic apparatus according to a first embodiment of the presently disclosed subject matter.

FIG. 1 is a block diagram illustrating an ultrasound diagnostic apparatus according to a first embodiment of the presently disclosed subject matter. An ultrasound diagnostic apparatus 10 illustrated in FIG. 1 transmits ultrasound beams from an ultrasound probe 300 to a object OBJ, receives ultrasound beams reflected by the object OBJ (hereinafter referred to as ultrasound echoes), and creates and displays an ultrasound image from a detection signal of the ultrasound echoes.

A CPU (Central Processing Unit) 100 controls the respective blocks of the ultrasound diagnostic apparatus 10 according to an operating input from an operating input unit 200.

The operating input unit 200 is an input device adapted to accept an operating input from an operator and includes a console 202 and a pointing device 204. The console 202 includes a keyboard for accepting an input of textual information (for example, patient information), a display mode changeover button for switching a display mode between a mode of independently displaying an amplitude image (B-mode image) and a mode of displaying the result of determining a local sound velocity value, a freeze button for instructing switching between a live mode and a freeze mode, a cine memory replay button for instructing the replay of a cine memory, and an analysis/measurement button for instructing the analysis/measurement of an ultrasound image. The pointing device 204 is used to accept an input for selecting a region on the screen of a display unit 104 and is, for example, a track ball or a mouse. Note that as the pointing device 204, a touch-sensitive panel can also be used.

A storage unit 102 is a memory unit for storing control programs for the CPU 100 to execute the control of the respective blocks of the ultrasound diagnostic apparatus 10 and is, for example, a hard disk or a semiconductor memory.

The display unit 104 is, for example, a CRT (Cathode Ray Tube) display or an LCD (Liquid Crystal Display), and displays ultrasound images (moving and still images) and various setup screens.

The ultrasound probe 300 is a probe abutted on the object OBJ when in use and includes a plurality of ultrasound transducers 302 constituting a one-dimensional or two-dimensional transducer array. Each ultrasound transducer 302 transmits ultrasound beams to the object OBJ on the basis of a drive signal applied from a transmitting circuit 402, and receives ultrasound echoes reflected from the object OBJ to output a detection signal.

Each ultrasound transducer 302 contains an oscillator configured by forming electrodes at both ends of a material having piezoelectricity (piezoelectric substance). As a piezoelectric substance composing the oscillator, piezoelectric ceramic, such as PZT (Pb (lead) zirconate titanate), or a polymer piezoelectric element, such as PVDF (polyvinylidene difluoride), can be used, for example. When an electrical signal is sent to the electrodes of the oscillator to apply a voltage thereto, the piezoelectric substance expands and contracts. The expansion and contraction of this piezoelectric substance generates ultrasound waves in each oscillator. For example, if a pulsing electrical signal is sent to the electrodes of the oscillator, pulsed ultrasound waves are generated and, if a continuous-wave electrical signal is sent to the electrodes of the oscillator, continuous ultrasound waves are generated. Ultrasound waves generated in the respective oscillators are synthesized to form ultrasound beams. In addition, when ultrasound waves are received by each oscillator, the piezoelectric substance of the oscillator expands and contracts, thereby generating an electrical signal. The electrical signal generated in each oscillator is output to a receiving circuit 404 as a detection signal of ultrasound waves.

Note that as the ultrasound transducers 302, it is possible to use elements of plural types different in ultrasound conversion method. For example, an oscillator including the abovementioned piezoelectric substance may be used as an element for transmitting ultrasound waves, and a photodetection method-based ultrasound transducer may be used as an element for receiving ultrasound waves. Here, the photodetection method-based ultrasound transducer is used to detect an ultrasound signal by converting the signal into an optical signal and is, for example, a Fabry-Perot resonator or a fiber Bragg grating.

Next, details on the respective blocks of the ultrasound diagnostic apparatus 10 will be described by taking, as an example, ultrasound diagnostic processing in a live mode. The live mode is a mode for performing the display, analysis and measurement of an ultrasound image (moving image) obtained by abutting the ultrasound probe 300 on the object OBJ and transmitting and receiving ultrasound waves.

When the ultrasound probe 300 is abutted on the object OBJ and ultrasound diagnosis is initiated by an instruction input from the operating input unit 200, the CPU 100 outputs a control signal to a transmitter/receiver unit 400 to cause the transmitter/receiver unit to begin transmitting ultrasound beams to the object OBJ and receiving ultrasound echoes from the object OBJ. The CPU 100 sets a direction of ultrasound beam transmission and the direction of ultrasound echo reception for each ultrasound transducer 302.

In addition, the CPU 100 selects a transmission delay pattern according to the direction of ultrasound beam transmission and selects a reception delay pattern according to the direction of ultrasound echo reception. Here, the transmission delay pattern refers to pattern data on delay time given to a drive signal, in order to form ultrasound beams in a desired direction by using ultrasound waves transmitted from the plurality of ultrasound transducers 302. The reception delay pattern refers to pattern data on delay time given to a detection signal, in order to extract ultrasound echoes from a desired direction by using ultrasound waves received by the plurality of ultrasound transducers 302. The transmission delay pattern and the reception delay pattern are previously stored in the storage unit 102. The CPU 100 selects a transmission delay pattern and a reception delay pattern from among the transmission delay patterns and reception delay patterns stored in the storage unit 102. According to the selected transmission delay pattern and reception delay pattern, the CPU 100 outputs a control signal to the transmitter/receiver unit 400 and performs the transmission/reception control of ultrasound waves.

The transmitting circuit 402 generates a drive signal according to the control signal from the CPU 100 and applies the drive signal to the ultrasound transducers 302. At this time, the transmitting circuit 402 delays a drive signal to be applied to each ultrasound transducer 302 on the basis of the transmission delay pattern selected by the CPU 100. Here, the transmitting circuit 402 performs transmission focusing for adjusting (delaying) a timing to apply a drive signal to each ultrasound transducer 302, so that ultrasound waves transmitted from the plurality of ultrasound transducers 302 form ultrasound beams. Note that the timing to apply a drive signal may be adjusted, in a manner that ultrasound waves transmitted at one time from the plurality of ultrasound transducers 302 reach the entire imaging region of the object OBJ.

The receiving circuit 404 receives and amplifies an ultrasound detection signal output from each ultrasound transducer 302, and outputs the signal to an A/D converter 406 as an analog RF signal.

The A/D (Analog-Digital) converter 406 converts the analog RF (Radio Frequency) signal output from the receiving circuit 404 into a digital RF signal (hereinafter referred to as RF data). Here, the RF data contains the phase information of a receiving wave (carrier wave). The RF data output from the A/D converter 406 is input to a signal processing unit 502, a cine memory 602 and a data analysis unit 700, respectively.

The cine memory 602 sequentially stores RF data input from the A/D converter 406. In addition, the cine memory 602 stores frame rate-related information (for example, the depth of a position where ultrasound waves are reflected, the density of scanning lines, and a parameter indicating the width of a visual field) input from the CPU 100 in association with the RF data.

As described above, since distances between respective ultrasound transducers 302 and an ultrasound reflection source within the object OBJ differ with each other, the time at which reflected waves arrive at respective ultrasound transducers 302 differ.

The signal processing unit 502 delays each RF data by an amount of time corresponding to a difference in the arrival time of reflected waves (delay time), according to a sound velocity (hereinafter referred to as a set sound velocity) or a sound-velocity distribution set on the basis of an ambient sound velocity input from a data analysis unit 700 to be described later. Next, the signal processing unit 502 performs a phase matching addition on the RF data to which the delay time has been given, thereby digitally performing reception focusing processing and generating RF image data.

If there are other ultrasound reflection sources in positions different from that of an ultrasound reflection source $X_{ROI}$, ultrasound detection signals from the other ultrasound reflection sources differ in arrival time. Consequently, an addition performed by the signal processing unit 502 causes the phases of the ultrasound detection signals from the other ultrasound reflection sources to cancel each other. This causes a reception signal from the ultrasound reflection source $X_{ROI}$ to be largest, and therefore, the reception signal comes into focus (reception focusing). Thus, RF image data in which a focus of ultrasound echoes is narrowed is formed by the reception focusing processing.

In addition, the signal processing unit 502 performs a distance-based attenuation correction to the RF image data by means of STC (Sensitivity Time Gain Control), according to the depth of reflection positions of ultrasound waves. After that, the signal processing unit 502 performs envelop detection processing, thereby generating B-mode image data (image data in which the amplitude of ultrasound echoes is represented by the brightness of points (luminance)).

The B-mode image data generated by the signal processing unit 502 is data obtained by a scanning method different from a commonly-used television signal scanning method. Accordingly, the DSC (Digital Scan Converter) 504 coverts (raster-converts) the B-mode image data into common image data (for example, image data for a television signal scanning method such as NTSC (National Television System Committee) method). The image processing unit 506 performs various types of necessary image processing (for example, gradation processing) on the image data input from the DSC 504.

An image memory 508 stores image data input from the image processing unit 506. A D/A converter 510 converts image data read out of the image memory 508 into an analog image signal and outputs the image signal to a display unit 104. Consequently, an ultrasound image (moving image) taken by the ultrasound probe 300 is displayed on the display unit 104.

Next, a cine memory replay mode will be described. The cine memory replay mode is a mode for displaying, analyzing and measuring an ultrasound diagnosis image on the basis of RF data stored in the cine memory 602.

When the cine memory replay button of the console 202 is pressed, the CPU 100 switches the operating mode of the ultrasound diagnostic apparatus 10 to the cine memory replay mode. When in the cine memory replay mode, the CPU 100 instructs a cine memory replay unit 604 to replay RF data specified by an operating input from an operator. The cine memory replay unit 604 reads RF data out of the cine memory 602, according to an instruction from the CPU 100, to transmit the RF data to the signal processing unit 502 of an image signal generation unit 500. The RF data transmitted from the cine memory 602 undergoes predetermined processing (the same processing as in live mode) at the signal processing unit 502, the DSC 504, and the image processing unit 506, so as to be converted into image data, and is then output through the image memory 508 and the D/A converter 510 to the display unit 104. Consequently, an ultrasound image (moving image or still image) based on the RF data stored in the cine memory 602 is displayed on the display unit 104.

If the freeze button of the console 202 is pressed while an ultrasound image (moving image) is being displayed in the live mode or the cine memory replay mode, the ultrasound image displayed when the freeze button is pressed is displayed on the display unit 104 as a still image. Consequently, the operator can observe a region of interest (ROI) on the still image.

When the measurement button of the console 202 is pressed, analysis/measurement specified by an operating input from the operator is performed. The data analysis unit 700 acquires RF data before the application of image processing from the A/D converter 406 or the cine memory 602 when the measurement button is pressed in each operating mode. Using the RF data, the data analysis unit 700 performs analysis/measurement specified by the operator (for example, analysis of strain in tissues (hardness diagnosis), bloodstream measurement, measurement of the movement of tissues, or IMT (Intima-Media Thickness) measurement.

In addition, the data analysis unit 700 calculates the ambient sound velocity of the region of interest and outputs the calculated ambient sound velocity to the signal processing unit 502. Details will be described later.

The results of analysis/measurement by the data analysis unit 700 are output to the DSC 504 of the image signal generation unit 500. The DSC 504 inserts the results of analysis/measurement by the data analysis unit 700 into the image data of the ultrasound image and outputs the ultrasound image to the display unit 104. Consequently, the ultrasound image and the analysis/measurement results are displayed on the display unit 104.

Figure 2:
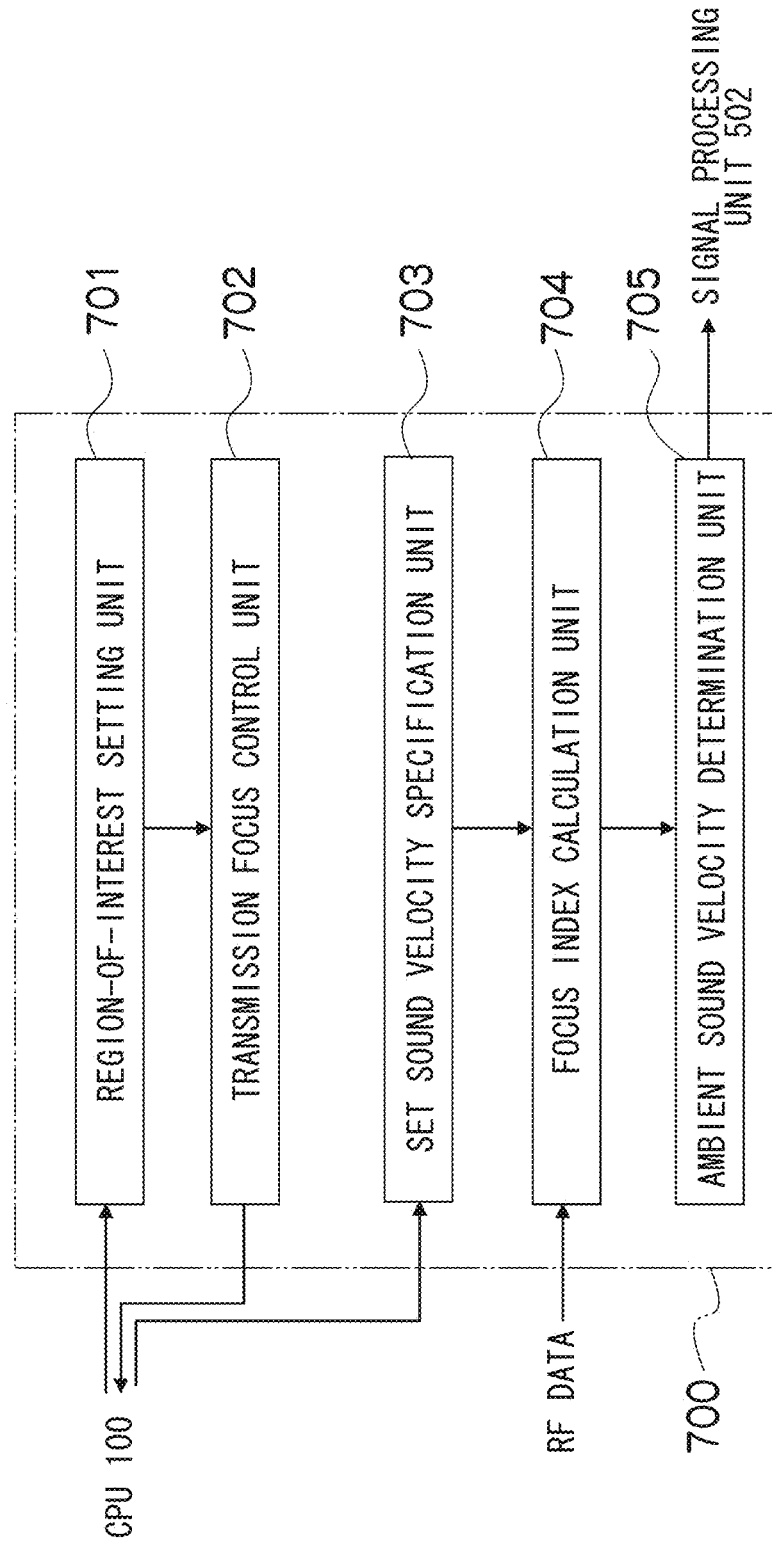
FIG. 2 is a block diagram illustrating the configuration of a data analysis unit of FIG. 1.

FIG. 2 is a block diagram illustrating the configuration of the data analysis unit of FIG. 1. The data analysis unit 700, as illustrated in FIG. 2, is configured by including a region-of-interest setting unit 701, a transmission focus control unit 702, a set sound velocity specification unit 703, a focus index calculation unit 704, and an ambient sound velocity determination unit 705.

The region-of-interest setting unit 701 is adapted to set a region of interest on an ultrasound image displayed on the display unit 104, according to an input by the operator from the operating input unit 200 through the CPU 100, and constitutes a region-of-interest setting device.

The transmission focus control unit 702 is adapted to give a transmission focus instruction to the CPU 100, so that the transmitting circuit 402 performs transmission focusing on the set region of interest, and constitutes a transmission focus instruction device.

The set sound velocity specification unit 703 is adapted to specify a set sound velocity used to perform reception focusing on RF data (ultrasound detection signal) on the basis of control by the CPU 100, and constitutes a set sound velocity specification device.

The focus index calculation unit 704 is adapted to read RF data out of the cine memory 602 and perform reception focusing on the RF data for each of the plurality of set sound velocities specified by the set sound velocity specification unit 703, thereby calculating the focus index of the RF data, and constitutes a focus index calculation device.

The ambient sound velocity determination unit 705 is adapted to determine the ambient sound velocity of a region of interest on the basis of a focus index for each of the plurality of set sound velocities, and constitutes an ambient sound velocity determination device.

Figure 3:
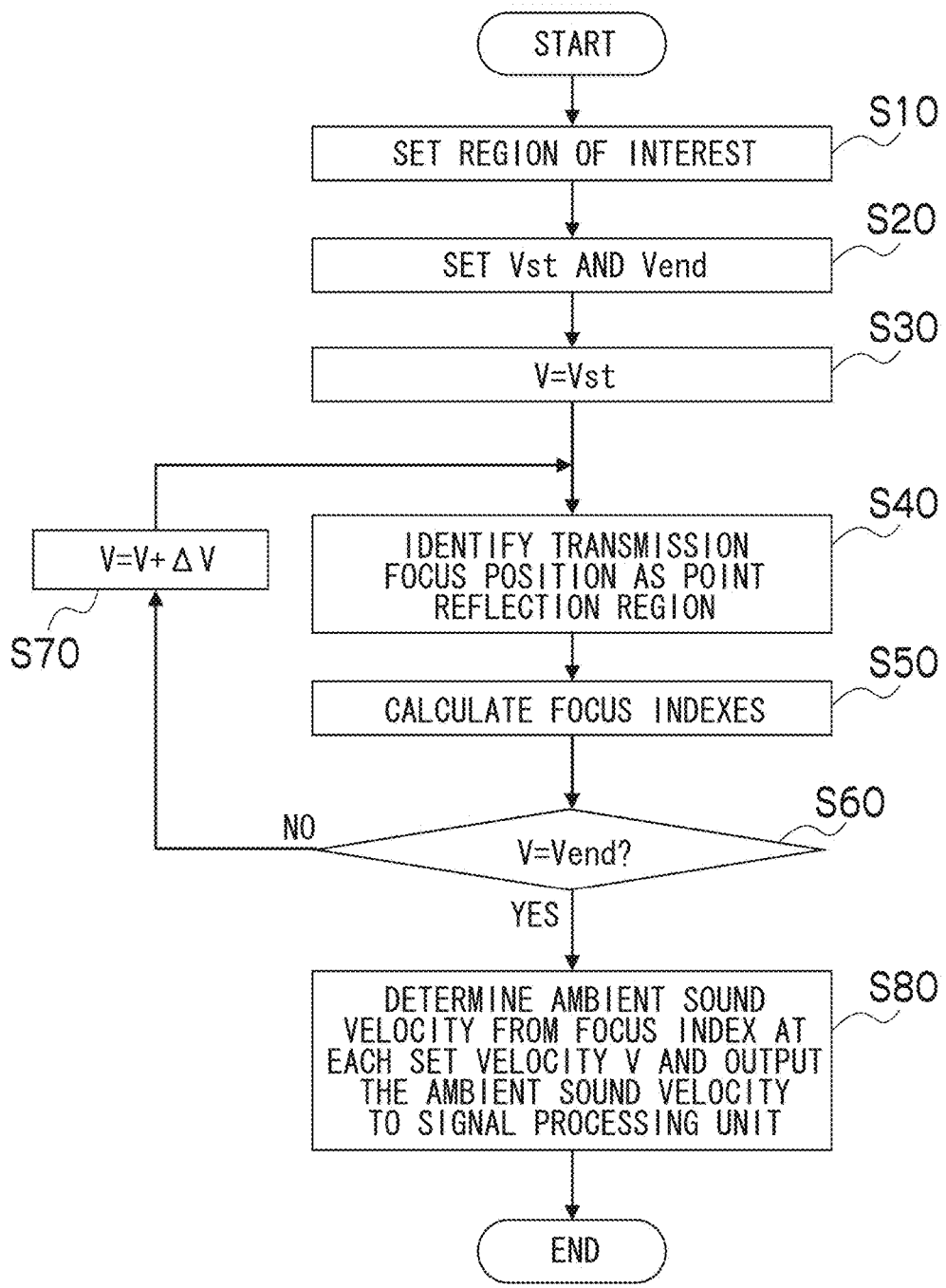
FIG. 3 is a flowchart illustrating a flow of processing by the data analysis unit of FIG. 2.

The operational effects of the present embodiment configured as described above will be described using the flowchart of FIG. 3. FIG. 3 is a flowchart illustrating a flow of processing by the data analysis unit of FIG. 2. In addition, FIGS. 4 to 7 are drawings used to explain the processing of FIG. 3.

As illustrated in FIG. 3, the data analysis unit 700 sets a region of interest on an ultrasound image displayed on the display unit 104 by the region-of-interest setting unit 701 according to an input by the operator from the operating input unit 200 through the CPU 100 (step S10).

Next, the data analysis unit 700 sets the starting sound velocity Vst and the ending sound velocity Vend of a set sound velocity V by the set sound velocity specification unit 703 (step S20), and sets the starting sound velocity Vst in the set sound velocity V (step S30).

Figure 4:
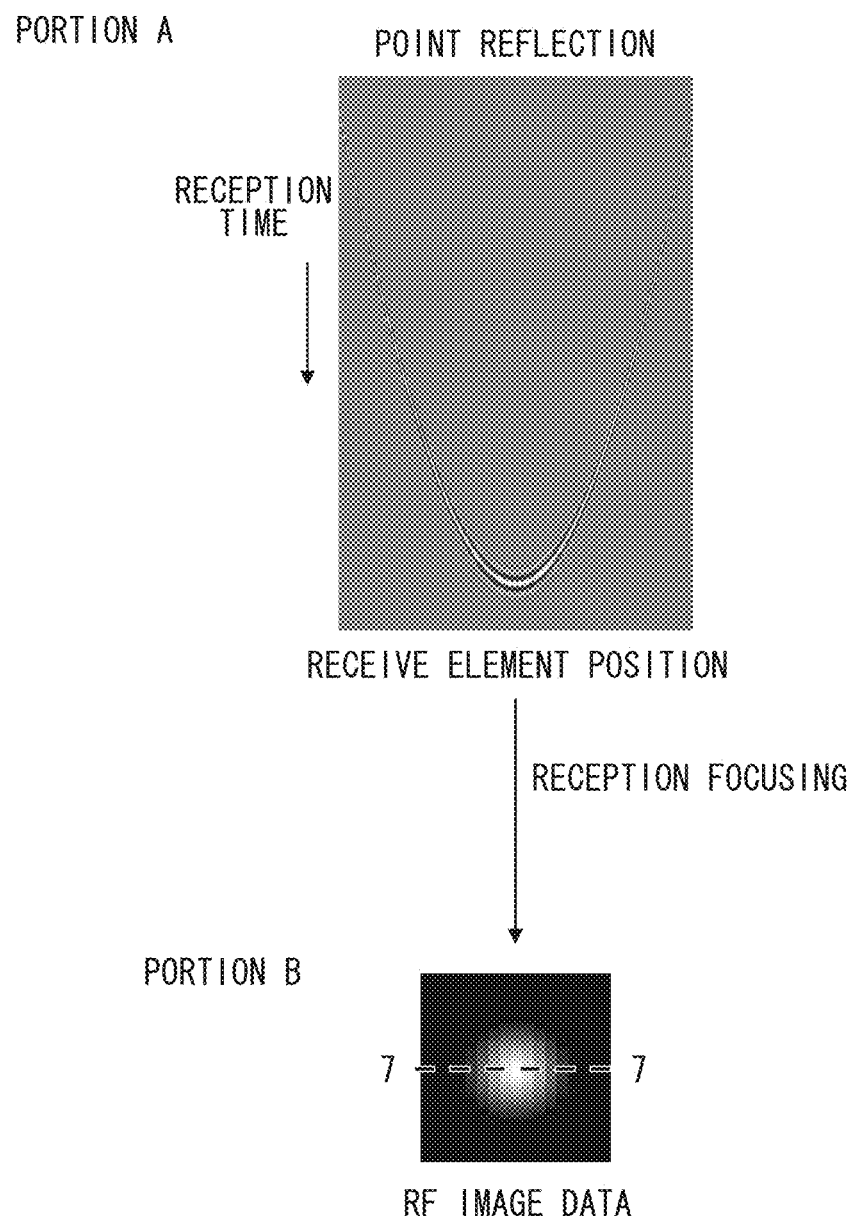
FIG. 4 is a first drawing used to explain the processing of FIG. 3.
Figure 5:
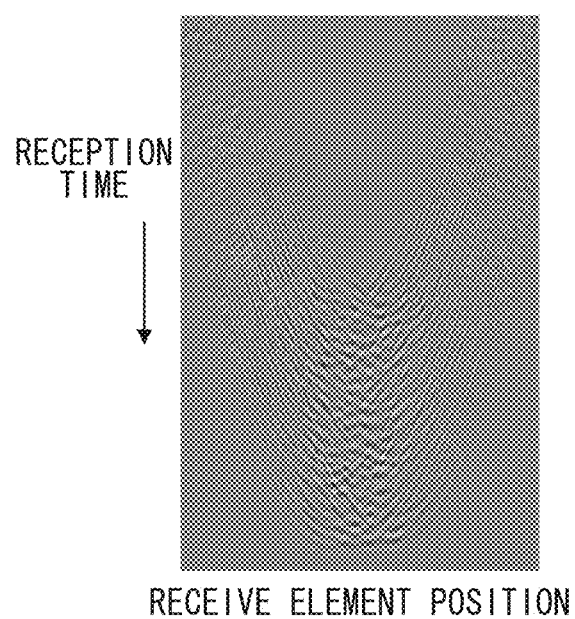
FIG. 5 is a second drawing used to explain the processing of FIG. 3.
Figure 6:
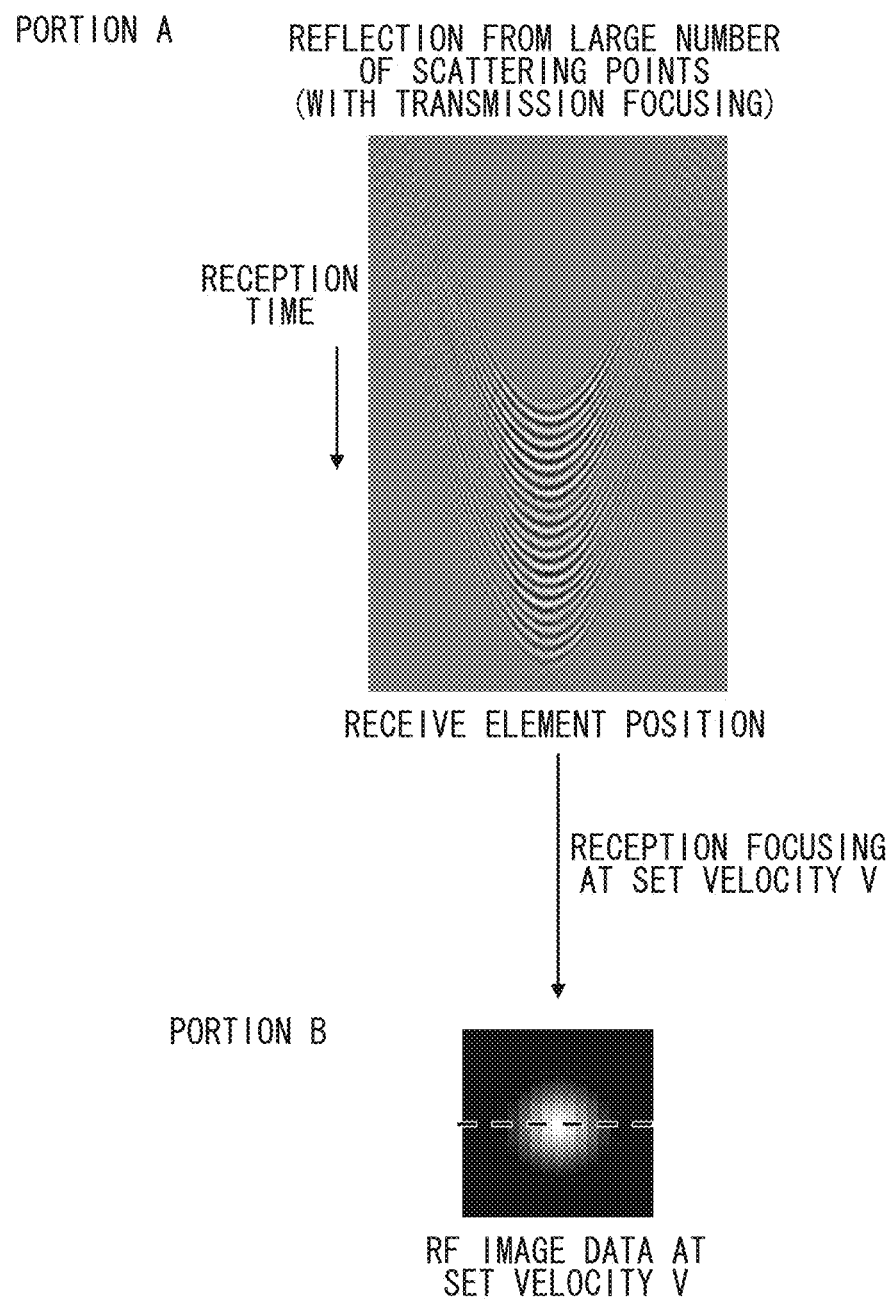
FIG. 6 is a third drawing used to explain the processing of FIG. 3.

FIG. 4 illustrates RF data obtained in case of point reflection. Portion A of FIG. 4 shoes an example of RF data and Portion B shows an RF image data of the RF data shown in Portion A. As illustrated in Portion B of FIG. 4, RF image data whose intensity and sharpness are analyzable, can be obtained for RF data from a region of point reflection when reception focusing is performed. On the other hand, in case of a large number of scattering points in a speckle region, a peak value and a spatial frequency in an azimuthal direction of RF data collapse due to interference (see FIG. 5). Therefore, it is difficult to obtain RF image data whose intensity and sharpness are analyzable when reception focusing is performed.

Hence, the data analysis unit 700 forms a pseudo-point reflection (see Portion A of FIG. 6) by applying transmission focusing to the large number of scattering points in the speckle region. Then, the data analysis unit 700 determines an ambient sound velocity also in the speckle region in the same way as in a point reflection region in which reception focusing is performed on an obtained receive element signal to analyze intensity and sharpness.

That is, the data analysis unit 700 gives a transmission focus instruction to the CPU 100, so that the transmitting circuit 402 performs transmission focusing on the region of interest set by the transmission focus control unit 702, in order to identify a transmission focus position as a pseudo-point reflection region (step S40).

Then, the data analysis unit 700 reads RF data out of the cine memory 602 by the focus index calculation unit 704, and performs reception focusing on RF data for each of the plurality of set sound velocities specified by the set sound velocity specification unit 703, in order to calculate the focus index of the RF image data (step S50).

Figure 7:
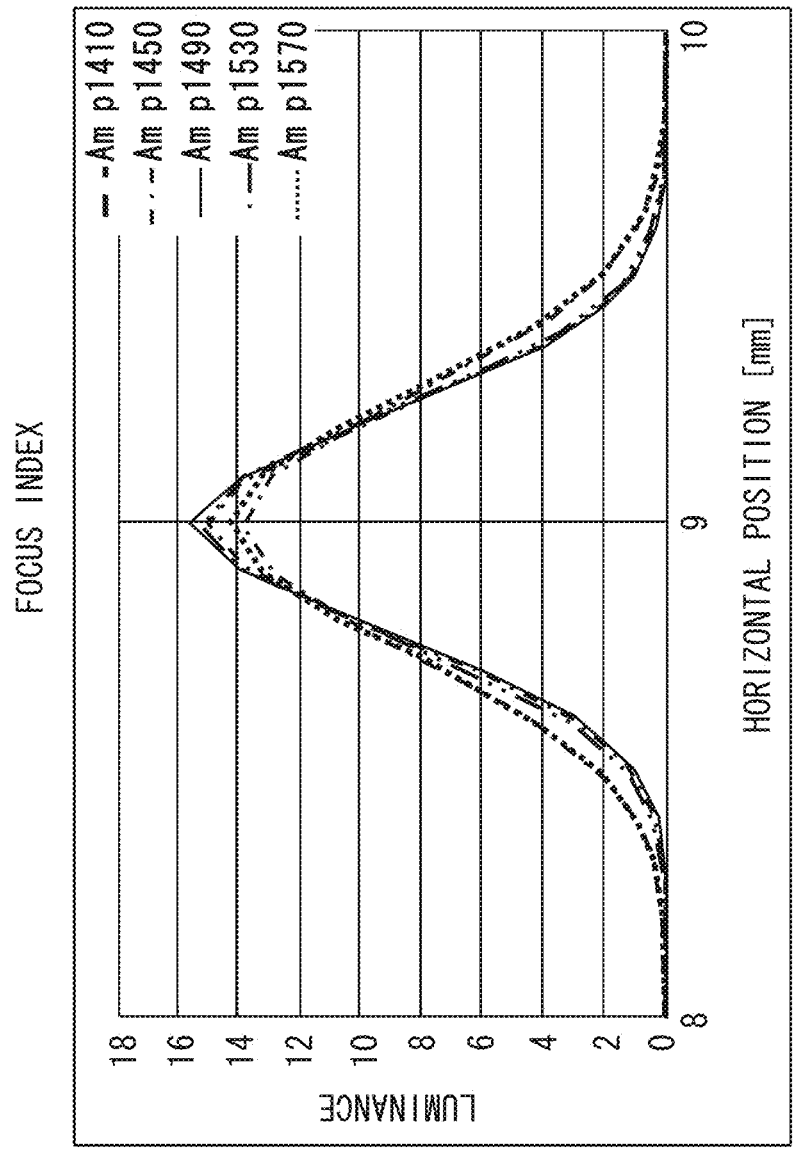
FIG. 7 is a fourth drawing used to explain the processing of FIG. 3.

FIG. 7 illustrates examples of profile of the RF image data (shown in FIG. 4) with set sound velocity varied. In the case of point-reflection RF image data illustrated in FIG. 4, a tendency of variation due to the set sound velocity is observed in the peak value and the spatial frequency in the azimuthal direction, as illustrated in FIG. 7. The tendency illustrated in FIG. 7 is also observed in the case of RF image data illustrated in FIG. 6 when a pseudo-point reflection region is formed by applying transmission focusing. Accordingly, the data analysis unit 700 calculates an integration value, a square integration value, a peak value, a contrast value, a half bandwidth, a frequency-spectral integration value, a frequency-spectral integration value or square integration value normalized by a maximum value or a DC (Direct Current) component, an autocorrelation value, and the like by the focus index calculation unit 704 as focus indexes (In FIG. 7, for example, Amp1410 indicates the amplitude when the set sound velocity is 1410. In the case of FIG. 7, the focus index is the maximum when set sound velocity is 1490 m/sec.).

Next, the data analysis unit 700 determines, by the set sound velocity specification unit 703, whether or not the set sound velocity V has reached the ending sound velocity Vend (step S60). If the set sound velocity V is less than the ending sound velocity Vend, the data analysis unit 700 adds a predetermined amount of step sound velocity ΔV to the set sound velocity V (step S70) and goes back to step S40. If a determination is made that the set sound velocity V has reached the ending sound velocity Vend, the data analysis unit 700 advances to step S80.

Then, the data analysis unit 700 determines the ambient sound velocity of the region of interest by the ambient sound velocity determination unit 705 in step S80, on the basis of a focus index for each of the plurality of set sound velocities. Then, the data analysis unit 700 outputs the determined ambient sound velocity to the signal processing unit 502 and terminates processing (in the case of FIG. 7, the set sound velocity Amp1490 of the highest focus index is determined as the ambient sound velocity).

As described above, in the present embodiment, transmission focusing is applied to an large number of scattering points in a speckle region to identify the region as a pseudo-point reflection region, a focus index for each of the plurality of set sound velocities is generated, and the ambient sound velocity of the region of interest is determined on the basis of the focus index for each of the plurality of set sound velocities. Thus, it is possible to correctly determine the ambient sound velocity of the region of interest including the speckle region at a point reflection level, thereby enabling the construction of a high-precision ultrasound image.

Second Embodiment

A second embodiment is the same in configuration as the first embodiment and differs therefrom only in processing at the data analysis unit. Therefore, only the difference will be described.

Figure 8:
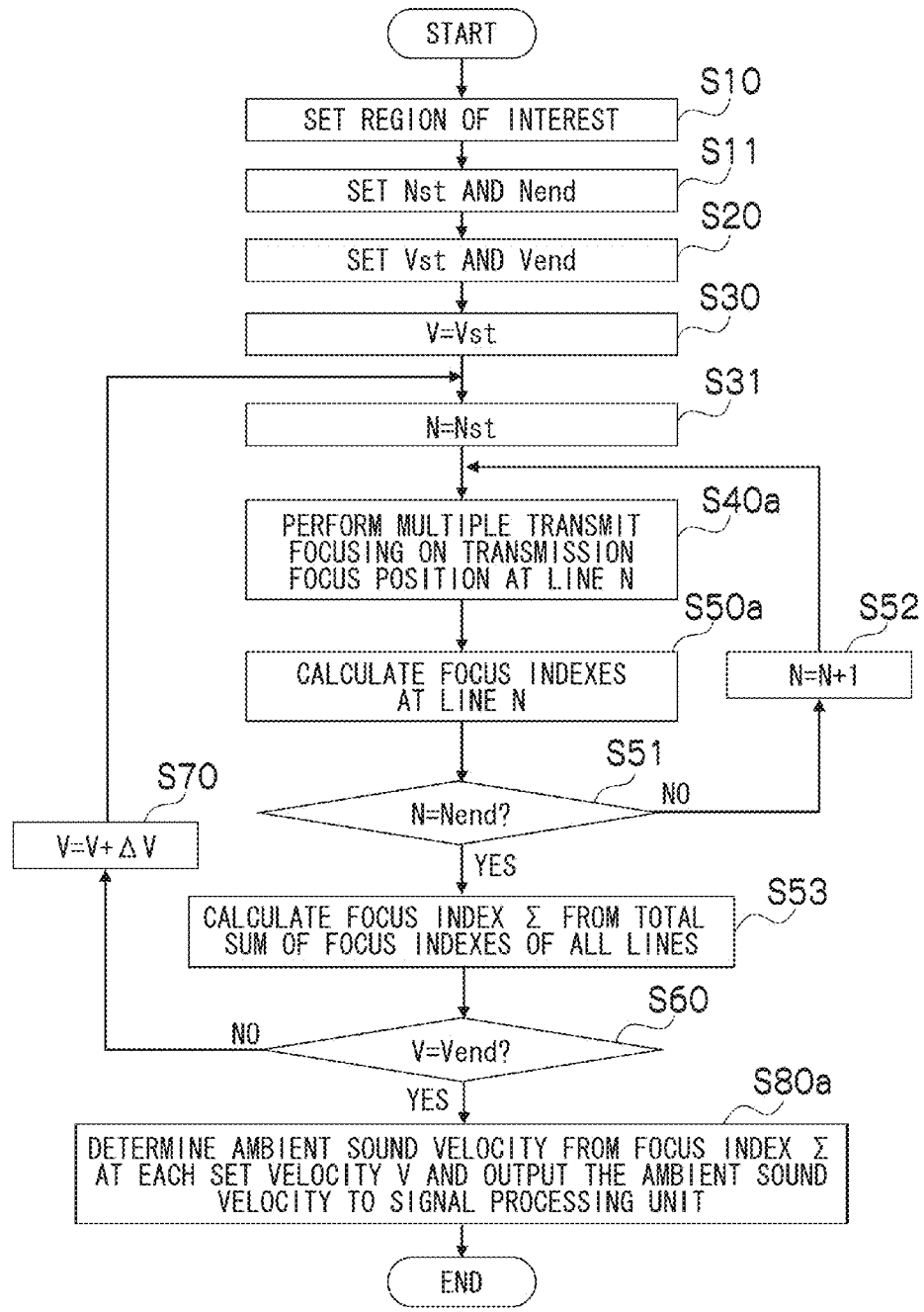
FIG. 8 is a flowchart illustrating a flow of processing by a data analysis unit according to a second embodiment of the presently disclosed subject matter.

FIG. 8 is a flowchart illustrating flow of processing by a data analysis unit according to the second embodiment of the presently disclosed subject matter. In addition, FIGS. 9 and 10 are drawings used to explain the processing of FIG. 8.

As illustrated in FIG. 8, a data analysis unit 700 sets the starting number Nst and the ending number Nend of a parameter N by a region-of-interest setting unit 701, following processing in step S10 (step S11). Then, the data analysis unit 700 sets the starting number Nst in the parameter N (step S31), following processing in step S30.

Figure 9:
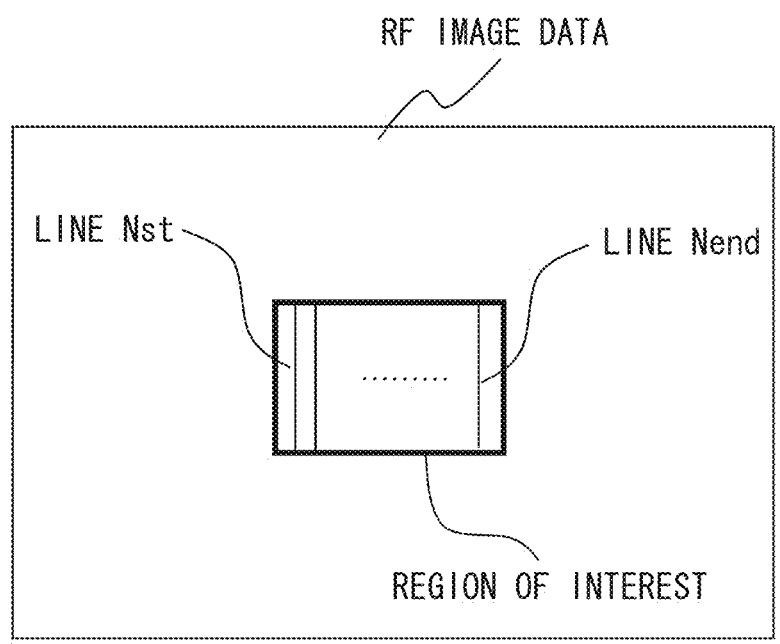
FIG. 9 is a first drawing used to explain the processing of FIG. 8.
Figure 10:
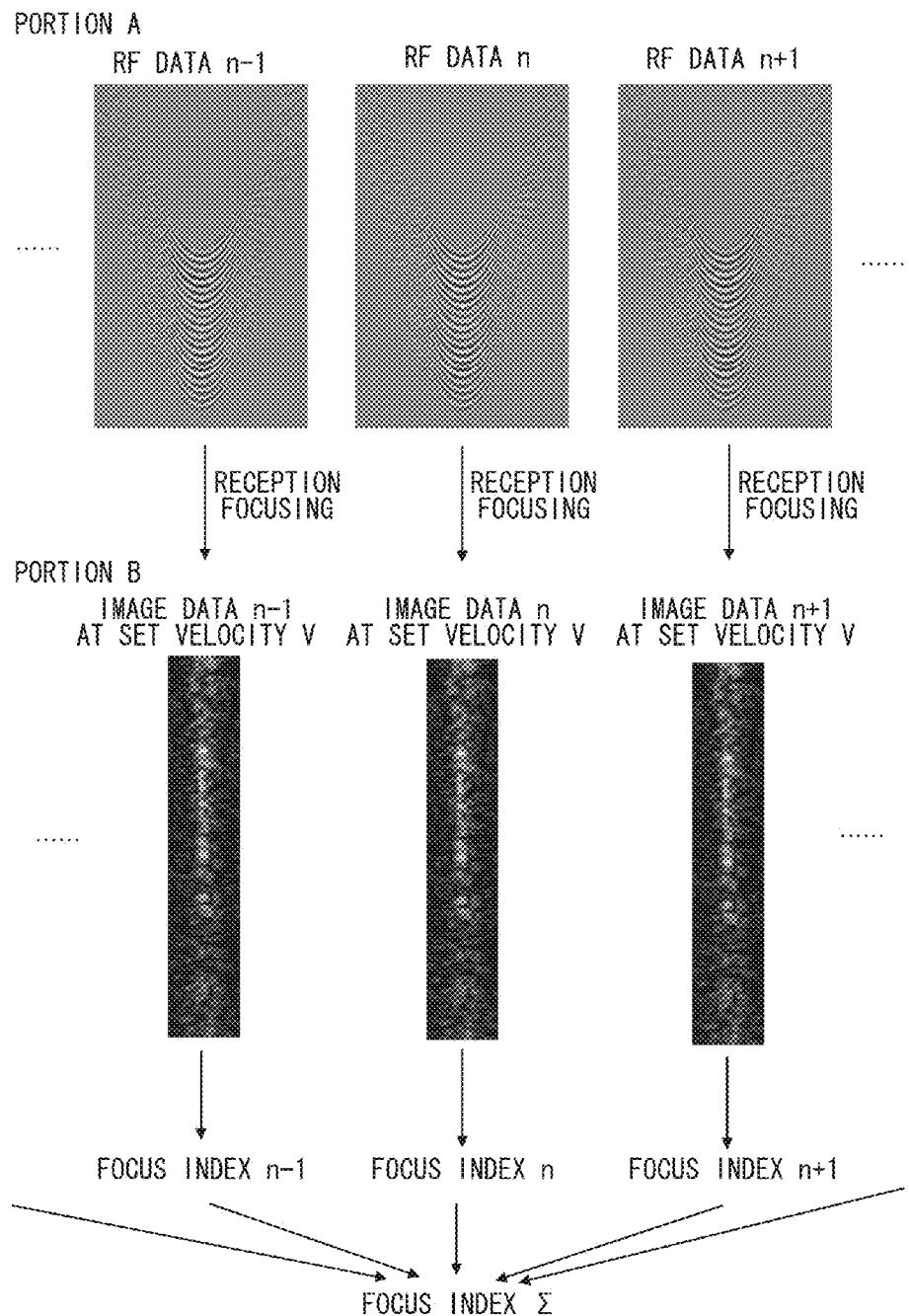
FIG. 10 is a second drawing used to explain the processing of FIG. 8.

In the present embodiment, when an operator specifies a region of interest for RF image data obtained by, for example, a line-by-line method, the data analysis unit 700 causes the region-of-interest setting unit 701 to set the region of interest, as illustrated in FIG. 9 (step S10). The data analysis unit 700 performs reception focusing with point reflection assumed, on receive element data obtained with respect to the respective lines of this region of interest, calculates focus indexes, and summates the respective lines and depths, thereby precisely evaluating an ambient sound velocity also in a speckle region.

Hence, the data analysis unit 700 gives a transmission focus instruction to the CPU 100, so that the transmitting circuit 402 performs transmission focusing on the region of interest set by the transmission focus control unit 702. Thus, the data analysis unit 700 identifies a position of transmission focusing as a pseudo-point reflection region and performs, for example, multiple transmit focusing (step S40*a*).

Then, the data analysis unit 700 reads the RF data of a line N (parameter N) out of a cine memory 602 by the focus index calculation unit 704, and executes reception focusing assumptive of point reflection on the RF data of the line N for each of the plurality of set sound velocities specified by the set sound velocity specification unit 703, thereby creating the RF image data of the line N and calculating focus indexes (step S50*a*). This RF image data is hereinafter referred to as a line image.

Next, the data analysis unit 700 determines, by the region-of-interest setting unit 701, whether or not the parameter N has reached the ending number Nend (step S51). If the parameter N is smaller than the ending number Nend, then the data analysis unit 700 increments the parameter N (step S52), and goes back to step S40*a*. If a determination is made that the parameter N has reached the ending number Nend, then the data analysis unit 700 advances to step S53.

Next, the data analysis unit 700 calculates a focus index Σ (=focus index of line Nst+focus index of line N(st+1)+ . . . ) from the total sum of the focus indexes of the line N (parameter N) at a set velocity V (step S53).

The data analysis unit 700 determines, by the ambient sound velocity determination unit 705, the ambient sound velocity of the region of interest on the basis of the focus index Σ for each of the plurality of set sound velocities, following the processing of steps S60 and S70, and outputs the determined ambient sound velocity to the signal processing unit 502, thereby terminating processing (step S80).

FIG. 10 illustrates the process for evaluating focus index Σ. Portion A of FIG. 10 shows RF image data for line n−1, line n and line n+1, obtained line-by-line basis. RF image data for lines are subject to reception focusing. Portion B shows RF image data for line n−1, line n and line n+1 at a set sound velocity of V, which are obtained after the reception focusing processing on the RF data shown in Portion A. Focus indexes for line n−1, line n and line n+1 are obtained from the RF image data for line n, line n−1, line n and line n+1, respectively, and then, the summation of these line-by-line focus indexes are obtained as the focus index Σ.

By the processing of FIG. 8 in the present embodiment, the data analysis unit 700 calculates focus indexes on a line-by-line basis, as illustrated in FIG. 10, from the RF image data based on line-by-line RF data resulting from multiple transmit focusing on the region of interest at the set velocity V which has been set. In addition, the data analysis unit 700 calculates the focus index Σ by summing these line-by-line focus indexes. Then, the data analysis unit 700 determines the ambient sound velocity of the region of interest from the focus index Σ evaluated for each set velocity V.

That is, in the present embodiment, reception focusing assumptive of point reflection is performed not only by using a transmission focus position but also by including points around the position, according to receive element data obtained on a line-by-line basis. Thus, an image is constructed, focus indexes are calculated, and the focus indexes of respective lines are summated, thereby obtaining a final focus index Σ and determining the ambient sound velocity of the region of interest.

As described above, according to the present embodiment, it is possible to even more precisely determine the ambient sound velocity of a region of interest due to the effect of smoothing focus indexes calculated from RF image data (line image) created by assuming point reflection with regard to respective lines constituting the region of interest, in addition to the advantageous effects of the first embodiment.

Also, according to the present embodiment, it is possible to more precisely determine the ambient sound velocity of a region of interest than a conventional method of evaluation from a line-by-line image. That is, in the case of point reflection illustrated in FIG. 4, RF image data varies in the peak value thereof in a transmission focus position corresponding to each line position, depending on a set sound velocity, as illustrated in FIG. 7. Both the conventional method in which only the RF image data of the transmission focus position is utilized and the method of the present embodiment in which the RF image data points including the transmission focus point and points around the transmission focus position is utilized are the same in accuracy. In the case of pseudo-point reflection illustrated in FIG. 6, however, a peak position and a profile more or less vary due to interference, though the RF image data exhibits the tendency shown in FIG. 7. Consequently, it is possible to precisely take over the tendency by utilizing the RF image data by including points around the transmission focus position. Thus, it is possible to determine the ambient sound velocity more precisely in the method of the present embodiment than in the conventional method.

Note that although a description has been made that the region of interest in each embodiment is set by an operator, the embodiments are not limited to this. For example, the region of interest can be made to automatically move over the RF image data shown in FIG. 9, so that the ambient sound velocities of all RF image data items can be determined on a region-of-interest basis.

In addition, although a description has been made that the data analysis unit 700 reads RF data out of the cine memory 602 by the focus index calculation unit 704 in step S50 or S50a of each of the above-described embodiments, the embodiments are not limited to this. Alternatively, the focus index calculation unit 704 may be made to perform reception focusing on RF data from the A/D converter 406 for each of the plurality of set sound velocities specified by the set sound velocity specification unit 703, thereby calculating the focus indexes of RF image data.

Third Embodiment

A third embodiment is configured to utilize only a frequency spectrum shape, without including image intensity, in order to determine an ambient sound velocity from a line image.

That is, by determining an ambient sound velocity only from a spatial frequency spectrum shape in an azimuthal direction, without including image intensity, for the above-mentioned line image (RF image data created by executing reception focusing assumptive of point reflection), it is possible to determine the ambient sound velocity of a speckle more precisely, compared with a conventional method for determining the ambient sound velocity from a line-by-line image.

Hereinafter, this mechanism will be described in detail.

In general, the point reflection (PSF) of an ultrasound image involves a variation in the characteristics of both "image intensity" and "frequency spectrum shape," depending on a set sound velocity, as has been already described using FIG. 7. Hence, the ambient sound velocity can be determined by taking advantage of this characteristic feature of dependence on the set sound velocity.

However, if an object of ultrasound diagnosis is a speckle, i.e., if there is any interference by ambient scatter, an error occurs in the above-described characteristic feature of dependence on the set sound velocity due to the interference for both the image intensity and the frequency spectrum.

In addition, a keen study made by the inventor of the presently disclosed subject matter has proved that which of image intensity and frequency spectrum is less liable to cause errors due to interference depends on PSF characteristics.

Specifically, it has proved that the frequency spectrum shape of PSF when only reception focusing is performed is less susceptible to interference than the image intensity of PSF and that, on the contrary, the image intensity of PSF resulting from the application of transmission focusing in addition to reception focusing is less susceptible to interference than the frequency spectrum shape of PSF.

Consequently, by utilizing an index based only on image intensity less susceptible to interference, for example, a "square sum" when a conventional line-by-line image subjected additionally to transmission focusing is utilized, it is possible to precisely determine the ambient sound velocity.

Here, the line-by-line image refers to an image formed by connecting the median lines of line images corresponding to the respective rounds of transmission.

Therefore, this index can be regarded as "an index obtained by smoothing a square sum of a plurality of median lines of line images."

Here, considering, for example, that a scattering point position does not always coincide with a median line (center of transmission focusing) in a line image, and therefore, a peak position of the image deviates from the median line due to interference, it is possible to correctly evaluate image intensity by utilizing "the contrast of line images," rather than by utilizing "the square sum of the median lines of line images." As a result, it is possible to precisely determine the ambient sound velocity.

Since the line image is an image in which only reception focusing is performed on a pseudo-point reflection region, it has proved that the frequency spectrum shape of PSF in that case is less susceptible to interference than the image intensity of PSF. Accordingly, it is understood that an ambient sound velocity can be determined more precisely by utilizing an index based only on a frequency spectrum shape, for example, "a square sum normalized by a mean value," "a frequency-spectral integration value normalized by a DC component (direct current component)," "an autocorrelation value," or "a frequency-spectral half bandwidth," than by utilizing "contrast" based on both image intensity and the frequency spectrum shape.

From the discussion heretofore made, it is understood that an ambient sound velocity can be precisely determined by utilizing an index based only on image intensity, such as a "square sum," when a common line-by-line image subjected additionally to transmission focusing is utilized. It can be said, however, that the ambient sound velocity can be determined more precisely by utilizing an index based only on a frequency spectrum shape, such as "a square sum normalized by a mean value," for a line image in which only reception focusing is performed on a pseudo-point reflection region formed by applying transmission focusing to a single point.

From Parseval's theorem, the "square sum normalized by a mean value" is the same as "the frequency-spectral square integration value normalized by a DC component." The square sum can be determined by simple calculations and is therefore practical.

When the ambient sound velocity is determined using a "square sum normalized by a mean value," it is possible to suppress noise-ridden, less-reliable edges of a line image by multiplying coefficients which become smaller in value toward the peripheral portions of the line image (RF image data) in which only reception focusing is performed on a pseudo-point reflection region formed by applying transmission focusing to a single point, as described above. In addition, since discontinuity can also be reduced, it is possible to improve the accuracy of the evaluated ambient sound velocity.

Figure 11:
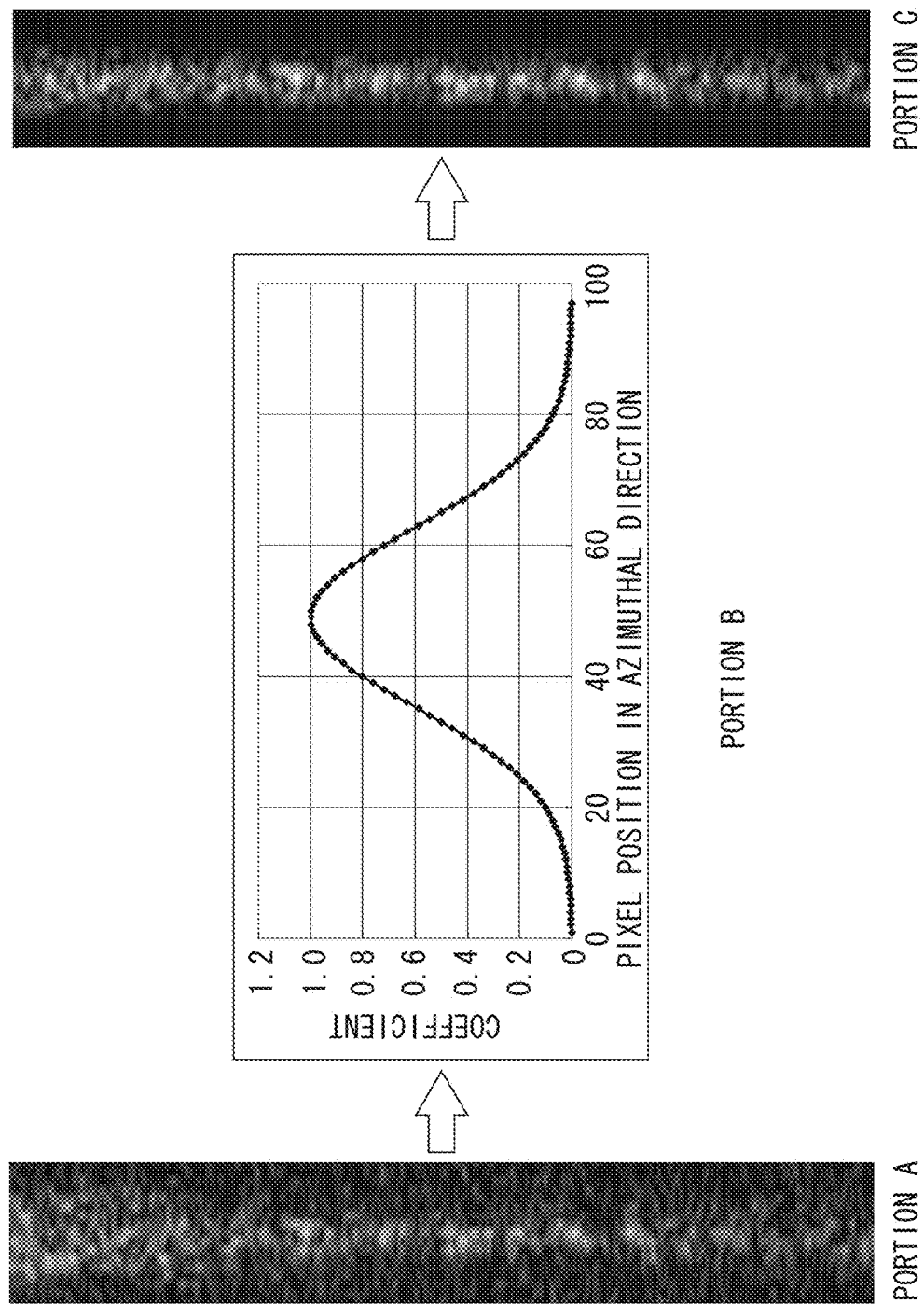
FIG. 11 is an explanatory drawing illustrating a situation in which a coefficient is multiplied, so as to suppress the values thereof toward the peripheral portions of a line image.

FIG. 11 illustrates this situation. In FIG. 11, an image in Portion A is a line image (RF image data for a line) and a graph in Portion B shows an image edge suppression coefficient. The graph of the image edge suppression coefficient is shown by plotting pixel positions in an azimuthal direction on the axis of abscissas and coefficients on the axis of ordinates. A coefficient value in the middle of the graph is 1, and coefficient values on both sides thereof are smaller than 1. Thus, the values of image edges (image periphery) are suppressed by multiplying these coefficient values. An image obtained by multiplying the line image in Portion A of FIG. 11 by the image edge suppression coefficient in Portion B of the graph is an image in Portion C. As shown by the image in Portion C, it is understood that the values of image edges are suppressed by multiplying coefficients.

Note that even if other indexes are used, suppressing the peripheral portions of a line image is also effective in improving the accuracy of the ambient sound velocity.

As has been described heretofore, according to the third embodiment, only frequency spectrum shape is utilized without including image intensity, in order to determine an ambient sound velocity from a line image. In particular, the third embodiment is configured to suppress less-reliable edges of a line image and multiply such a coefficient as to become smaller in value toward the edges of the image, in order to reduce discontinuity. Consequently, it is possible to further improve the accuracy of an ambient sound velocity to be evaluated.

Note that if a region of interest is not a uniform speckle but includes a distinct structural object therein at the time of determining the ambient sound velocity of the region of interest, such a method for determining an ambient sound velocity by utilizing a line image and using only a frequency spectrum shape as described above in the third embodiment may rather cause accuracy degradation. That is, even if transmission focusing is applied to the median line of a line image, errors may occur if reflection from neighboring lines is too strong.

As described above, if any distinct structural object is included within the region of interest, it is desirable to determine an ambient sound velocity by utilizing a conventional line-by-line image rather than by utilizing a line image. Since the line-by-line image is an image to which transmission focusing has been applied, the ambient sound velocity can be determined precisely by utilizing an index based on image intensity, for example, a "square sum".

Hence, as a fourth embodiment, a description will be given next of a method for separating a process as to what index to use thereafter in order to evaluate an ambient sound velocity by determining whether or not any structural object is included in a region of interest.

Fourth Embodiment

As methods for determining whether or not any structural object is included in the region of interest, that is, whether or not the speckle in question is uniform, the following three methods, for example, are conceivable:

A first method is to make a determination according to whether or not a ratio of the number of pixels larger than predetermined multiples of a mean value to the total number of pixels within the region of interest is higher than a predetermined threshold value.

A second method is to make a determination according to whether or not there is a pixel whose first-order derivative value in a depth direction before or after logarithmic compression is greater than a predetermined threshold value.

A third method is to make a determination according to whether or not the degree of deviation from a Rayleigh distribution is greater than a predetermined threshold value.

In addition, as a method of determination based on the degree of deviation from the Rayleigh distribution, the following method, for example, is conceivable:

That is, a relationship between the standard deviation $\sigma$ and the mean value u of the Rayleigh distribution is given by the following equation.

$$\sigma = \text{sqrt}(4/\pi - 1) * u$$

where sqrt ( ) is a square root of a term within the parentheses ( ).

At this time, the value of $\sigma$ becomes large if any structural object is included in the region of interest. Consequently, a determination can be made according to whether or not a ratio of a virtual standard deviation $\sigma 0$ obtained from the mean value of the region of interest by using the above-described equation to the actual standard deviation $\sigma$ is higher than a predetermined threshold value.

By using any one of the above-described methods, a determination is made first as to whether or not any structural object is included in the region of interest, i.e., whether the speckle in question is uniform or not uniform.

Next, if a determination is made consequently that, for example, no structural objects are included in the region of interest, a line image is utilized to evaluate an ambient sound velocity by using an index based only on a frequency spectrum shape, without including image intensity, as in the above-described third embodiment.

On the other hand, if a determination is made that a structural object is included in the region of interest, a line-by-line image is used to evaluate an ambient sound velocity, as in a conventional method. At this time, the ambient sound velocity is evaluated by using an index based only on the intensity information of that line, for example, at least one of an integration value, a square integration value, a peak value, and a frequency-spectral integration value, without including lines around the median line of the image.

As has been described heretofore, according to the fourth embodiment, a determination is made as to whether or not any structural object is included in the region of interest, i.e., whether or not the region is a uniform speckle region. Then, an ambient sound velocity is evaluated using an index according to the result of determination. In particular, if any structural object is not included in the region of interest, a line image is utilized to evaluate the ambient sound velocity by using an index based only on a frequency spectrum shape, without including image intensity. Conversely, if a structural object is included in the region of interest, a commonly-used image (line-by-line image) is utilized to evaluate the ambient sound velocity, rather than utilizing a line image. Thus, it is possible to further improve the accuracy of the ambient sound velocity.

While an ultrasound diagnostic apparatus and the signal processing method thereof of the presently disclosed subject matter have been heretofore described in detail, the presently disclosed subject matter is not limited to the above-described embodiments. Accordingly, it is needless to say that various improvements and modifications may be applied to the presently disclosed subject matter without departing from the subject matter thereof.

What is claimed is:

1. An ultrasound diagnostic apparatus comprising:
    an ultrasound probe including a plurality of ultrasound transducers configured to transmit ultrasound waves to an object, and configured to receive ultrasound waves reflected by the object and to generate ultrasound detection signals;
    a display unit configured to display a first ultrasound image;
    a region-of-interest setting unit configured to set a region of interest on the first ultrasound image;
    a storage unit configured to store a plurality of transmission delay patterns;
    a processor configured to select a transmission delay pattern from among said plurality of stored transmission delay patterns;
    a transmitting circuit configured to generate a drive signal and supply the drive signal to said plurality of ultrasound transducers based on the selected transmission delay pattern, thereby performing transmission focusing and causing the ultrasound waves to be transmitted to said region of interest based on said drive signal using the plurality of ultrasound transducers;
    a receiving circuit which receives said ultrasound detection signals, and outputs said ultrasound detection signals to an analog/digital (A/D) converter as an analog Radio Frequency (RF) signal;
    wherein said A/D converter converts said analog RF signal from the receiving circuit into RF data;
    an image signal generation unit which processes said RF data from said A/D converter, performs image processing, and generates a second ultrasound image;
    a data analysis unit which acquires said RF data from said A/D converter before application of said image processing by said image signal generation unit, and determines an ambient sound velocity of the set region of interest by calculating a focus index of said RF data;
    wherein said ambient sound velocity of said set region of interest enables construction of said second ultrasound image;
    wherein the ambient sound velocity is calculated by multiplying said focus index by image edge suppression coefficients that become smaller in value toward peripheral portions of said RF data.

2. The ultrasound diagnostic apparatus according to claim 1, wherein said focus index is calculated based on a frequency distribution of said ultrasound detection signals in an azimuthal direction of said RF data.

3. The ultrasound diagnostic apparatus according to claim 1, further including:
    an ultrasound image construction device configured to construct said second ultrasound image on a basis of said ambient sound velocity of said set region of interest.

4. A signal processing method of an ultrasound diagnostic apparatus, comprising:
    displaying a first ultrasound image;
    setting a region of interest on the displayed first ultrasound image;
    performing transmission focusing on the region of interest by generating a drive signal from a transmitting circuit, based on a transmission delay pattern selected by a processor from among a plurality of stored transmission delay patterns, and transmitting ultrasound waves to said region of interest based on said drive signal using a plurality of ultrasound transducers;
    using the plurality of ultrasound transducers to receive ultrasound waves reflected by the region of interest to output ultrasound detection signals;
    using a receiving circuit to receive said ultrasound detection signals from said plurality of ultrasound transducers and to output said ultrasound detection signals to an analog/digital (A/D) converter as analogue Radio Frequency (RF) signals;
    using the A/D converter to convert the RF signals output from the receiving circuit into RF data;
    generating a second ultrasound image using an image signal generation unit which processes said RF data from said A/D converter and performs image processing;
    using a data analysis unit to acquire said RF data from said A/D converter before application of said image processing by said image processing generation unit, and to determine an ambient sound velocity of the region of interest by calculating a focus index of said RF data;
    wherein the determined ambient sound velocity enables construction of said second ultrasound image;
    wherein the ambient sound velocity is calculated by multiplying said focus index by image edge suppression coefficients that become smaller in value toward peripheral portions of said RF data.

* * * * *